United States Patent [19]

Hon et al.

[11] Patent Number: 4,993,422
[45] Date of Patent: Feb. 19, 1991

[54] APPARATUS FOR MEASURING BLOOD PRESSURE

[75] Inventors: Edward H. Hon; Edward D. Hon, both of Bradbury, Calif.

[73] Assignee: The Hon Group, Encino, Calif.

[21] Appl. No.: 287,715

[22] Filed: Dec. 19, 1988

Related U.S. Application Data

[63] Continuation of Ser. No. 858,713, May 2, 1986, abandoned, which is a continuation-in-part of Ser. No. 780,398, Sep. 26, 1985.

[51] Int. Cl.⁵ .............................................. A61B 5/021
[52] U.S. Cl. ...................................... 128/672; 128/690
[58] Field of Search .......................... 128/672, 677–683, 128/687–690, 877

[56] References Cited

U.S. PATENT DOCUMENTS

| 3,102,534 | 9/1963 | Bigliano et al. | 128/672 |
| 3,123,068 | 3/1964 | Bigliano | 128/672 |
| 3,219,035 | 11/1965 | Pressman et al. | 128/672 |
| 3,299,882 | 1/1967 | Masino | 128/687 X |
| 3,880,145 | 4/1975 | Blick | 128/672 |
| 4,030,484 | 6/1977 | Kuska et al. | 128/672 |
| 4,369,774 | 1/1983 | Robbins | 128/877 |
| 4,423,738 | 1/1984 | Newgard | 128/672 |

Primary Examiner—Angela D. Sykes
Attorney, Agent, or Firm—Lewis Anten

[57] ABSTRACT

Apparatus for continuously measuring blood pressure, preferably in the situs of the wrist is disclosed. A hand and wrist support structure maintains the hand and wrist in a substantially fixed relationship. A pressure monitoring apparatus consisting of a sensing device and structure for maintaining the sensor over the radial artery of a user so as to measure the blood pressure is disclosed.

17 Claims, 5 Drawing Sheets

APPARATUS FOR MEASURING BLOOD PRESSURE

CROSS REFERENCE TO RELATED APPLICATION

This is a continuation of application Ser. No. 858,713, filed on May 2, 1986, now abandoned which is a continuation-in-part of application Ser. No. 780,398 filed on Sept. 26, 1985, pending.

BACKGROUND OF THE INVENTION

This invention relates to an apparatus for continuously and non-invasively measuring blood pressure.

In particular, the invention finds use as part of a general system for measurement of blood pressure based on repetitive evaluation of the pressure fluctuation, and in particular the patterns of the radial artery and therefore reflects the arterial blood pressure of the general circulation.

The apparatus of the present invention enables continuous monitoring of blood pressure patterns over extended periods of time. This is needed in the evaluation of circulatory function and ambulatory monitoring of cardiac function, and is useful for hypertension studies and for obtaining records of circulation.

In the past, various artery occlusion procedures have been used, stopping blood flow in radial, brachial, dorsalis pedis, temporal and other arteries to estimate blood pressure, particularly of the central circulatory system. Data thus obtained is by its very nature discontinuous.

It has been possible to insert pressure sensing devices and/or catheters temporarily into the arteries of the circulatory system for direct continuous measurements (invasive method of measuring). While intra-arterial catheterization may provide more precise measurements of blood pressure than arterial occlusion devices, the pressure measured is likely to be more related to the central circulation, than of the peripheral circulation. Also, the blood pressure measurements and patterns thus obtained are likely to be altered by the traumatic operation of inserting the catheter, by the drug administered so that the catheter can be inserted, and by the presence of a foreign body in the circulatory system.

The principal non-invasive blood pressure measuring device used today is an auscultatory system where a cuff pressure is applied to occlude a major artery, such as the brachial artery. In practice, an inflatable encircling cuff is placed around the arm and inflated to occlude the major artery, e.g., brachial, to prevent flow of blood in the artery. As the pressure in the cuff is slowly lowered, permitting flow of blood in the artery, Korotkoff sounds are heard. The cuff pressure at which the first sound is heard is defined as the systolic pressure. The pressure in the cuff is then lowered further the pressure in the cuff at which the sound fades is defined as the diastolic pressure.

A second occluding cuff technique uses palpation of the pulse rather than auscultation. In this palpatory system, as the occluding cuff pressure is slowly released, arterial pulsations are detected by palpation. The pressure level of the cuff at which the pulsations are first perceived is designated as systolic blood pressure. Diastolic blood pressure cannot be detected by palpation.

Another occluding cuff system uses the maximum and minimum oscillations of arterial blood pressure as referenced to cuff pressure as indications of systolic and diastolic blood pressure, respectively. In addition to being an intermittent, occlusive technique, the measurements thus obtained are likely influenced by the limb volume of the limb around which the cuff is applied.

It can be generally stated that all blood pressure measurements which are based upon arterial occlusion are inherently discontinuous, needing to be repeated, at best, from time to time. Such measurements cannot resolve blood pressure patterns on a beat to beat basis, or show the wave form of the individual pulses.

Thus, although the current method of auscultatory measurement of brachial blood pressure is by far the most widely used technique for blood pressure measurement, the technique is relatively imprecise, since the observed values vary from observer to observer and the very act of taking blood pressure itself causes a momentary change in blood pressure. Additionally, since the occlusion itself is known to have physiological and psychological effects, the measurements may be distorted.

A non-invasive, non-occlusive approach to the measurement of blood pressure would have many advantages. Unfortunately, prior techniques for this purpose have been found to have disadvantages. Those directed at measuring arterial pressure by placing a transducer directly over a partially compressed radial or dorsalis pedis artery can, under optimum circumstances, provide accurate records for short periods of time. Considerable difficulty is experienced in maintaining constant mechanical coupling between the tissue overlying the artery and pressure on the arterial wall during even the slightest patient motion.

An example of this type of measuring system is disclosed in U.S. Pat. No. 3,880,145 to E. F. Blick, issued Apr. 29, 1975. Blick described a system using a strain gauge to flatten the radial artery at the inside of the wrist. A second sensor is mounted cutaneously alongside but away from the artery. The signal from the second sensor is subtracted from that sensor associated with the flattened artery. In practice, the signal from the radial artery sensor contains arterial pulsations as well as "noise". The noise which is measured by the cutaneous transducer is subtracted from the former signal, leaving a measurement of the arterial pulsations alone. Such systems are complex and during patient movement it is very difficult to precisely match the "noise" component arising from both sensors.

Another such device is shown in the patent to Iberall, U.S. Pat. No. 3,704,708, in which a sensing device is placed over a vascular duct, with the duct being flattened and the invention is limited to use on a vascular duct which is near the surface of the body. In the preferred embodiment, the sensor is held in direct contact with the vascular duct by use of a band around the head.

A general discussion and review of various previously proposed systems for blood pressure monitoring is given in the book, "The Direct and Indirect Measurement of Blood Pressure," by L. A. Geddes (Year Book Medical Publishers, Chicago, 1970) where a number of blood pressure techniques are outlined (see pages 37, 71, 87 and 96).

It has been demonstrated that there is a hitherto unfulfilled need for a sensitive, continuous, noninvasive, non-occlusive measuring technique for recording blood pressure measurements and beat to beat patterns undistorted and uninterrupted by the measuring system, per se. The method and the apparatus of the present invention enables non-invasive, non-occlusive continuous measurements over extended periods of time. Continuous information of this type is essential for adequate evaluation of cardiac and vascular function. It is of particular importance in the diagnosis and treatment of hypertension, since it provides detailed information concerning the peripheral circulation not available heretofore.

SUMMARY OF THE INVENTION

The apparatus of the present invention continuously measures blood pressure with a strain gauge or pressure transducer, (or similar measuring device) held against an artery, in the preferred embodiment the radial artery, with a wrist and hand support structure for immobilizing and maintaining the hand and forearm at an open, fixed relationship to one another, at an angle of about 20°, to cause the radial artery to be forced to the surface of the wrist.

A major use of the apparatus is to provide continuous blood pressure measurements and patterns of blood pressure in the radial artery. To maintain mechanical stability of the strain gauge in relation to the radial artery, a substantially rigid support platform forms a holder that encircles the wrist for the sensor gauge.

In the strain gauge or transducer assembly an isolating ring surrounds the active portion of the gauge pressed against the wrist of the user above the radial artery. This isolation ring projects beyond the measuring surface of the strain gauge and serves to substantially isolate the portion of the skin above the radial artery from extraneous effects and reduce noise emanating from adjacent tissue.

The isolating ring also causes a portion of the skin captured by the ring to protrude into the chamber formed by the side walls of the ring and the active surface of the strain gauge (or other pressure measuring device) whose measuring surface is thus tangentially oriented to the slightly domed segregated tissue or skin. The isolating ring essentially surrounds the circumference of the bottom of the strain gauge. The long axis of the strain gauge or transducer is normal to the wrist.

Together, the ring and lower portion of the strain gauge form an inverted shallow dish in which the inside circumference of the ring forms the peripheral walls and the bottom measuring surface of the strain gauge its bottom. Consequently, when the strain gauge assembly is pressed against the tissue and the radial artery, the skin fills the space between the ring and the strain gauge measuring surface.

If the surface area of the gauge in contact with the skin is small in relationship to the area enclosed by the isolating ring, the trauma to the cutaneous tissue felt by the user is greatly reduced, and consequently, the apparatus can be maintained for longer periods of time without discomfiture to the user.

The blood pressure changes in this portion of the tissue or skin resulting from the pressure changes in the radial artery are detected by the strain gauge and can be observed as a continuous pattern on an oscilloscope or recorded in a conventional manner, such as on a strip chart or magnetic tape. Although the major component of the wave form is a result of the pressure changes in the radial artery, a relatively small portion of the wave form is the component representing the blood pressure changes in the cutaneous tissue in contact with the strain gauge.

The magnitude of the recorded blood pressure changes are affected not only by the change within the isolated cutaneous tissue, but also by the forces which are holding the isolating ring against the tissue. The radial artery is not surrounded by a rigid bone structure by itself so that it can be encircled and tightened to hold a strain gauge, without being so tight that it is uncomfortable and closes off circulation in the wrist. Once the strain gauge is fixed relative to the radial artery, the pressure is applied to the gauge by a spring assembly. In order to keep these forces sufficiently constant, the strain gauge assembly must be attached to a stabilizing platform in a substantially rigid, mechanical manner, so as to prevent the strain gauge from moving and providing inaccurate readings. This is achieved by placing the strain gauge in a structure that rigidly encircles the wrist. In such a position, the hand and wrist are held in a stable position, forming a stable platform for the strain gauge.

In practice, the initial pressure may be adjusted so that the observed blood pressure is a given number of mms Hg below the brachial systolic blood pressure, if the latter is used as a reference point. Alternatively, a predetermined known coupling pressure may be applied to the non-active end of the strain gauge assembly by mechanical means, such as a calibrated spring, by pneumatic means, or directly by a rigid rod where the coupling pressure is measured by another strain gauge or other pressure sensing device. In situations where known coupling pressures are used, blood pressure changes may be referenced to them, as well as to the clinically determined brachial blood pressure.

Since mechanical stability is highly desirable, further stabilization may be achieved by using doublesided adhesive or other adhesive non-slipping materials on the interior surface of the stabilizing structure proximate the wrist.

When the foregoing non-invasive, non-occlusive technique is used as described, it is possible to continuously make cutaneous blood pressure measurements and record patterns under most clinical circumstances including in particular for women during labor, where it is ordinarily expected that the patient will not be maintaining a relatively inactive position.

OBJECTS OF THE INVENTION

In general, it is an object of the present invention to provide an apparatus for making measurement of blood pressure which will overcome the disadvantages of the prior art.

A further object is to provide an apparatus of the above character which does not require complete immobility of the patient and which provides a continuous, non-invasive blood pressure measurement.

A further object is to provide an apparatus of the above character which is sufficiently sensitive so as to record changes in the patterns of the arterial system due to the application of medication and other conditions that would be expected to cause changes in the cardiovascular system, as reflected in the radial artery pressure patterns.

It is a further object of the present invention to provide for a non-invasive, non-occlusive blood pressure evaluation technique that will provide permanent records of momentary changes in blood pressure, and make it possible to evaluate even the evanescent effects of interacting neurocirculatory reflexes.

It is yet another object of the present invention to provide a system that is inexpensive to manufacture and easy to use in association with equipment presently widely used by physicians.

It is a further object of the present invention to provide apparatus that may be used with equal ease on the left wrist or the right wrist of the user.

These and other objects and features of the invention will become apparent from the following description and claims when taken in conjunction with the accompanying drawings, of which:

DETAILED DESCRIPTION OF THE INVENTION

Figure 1:
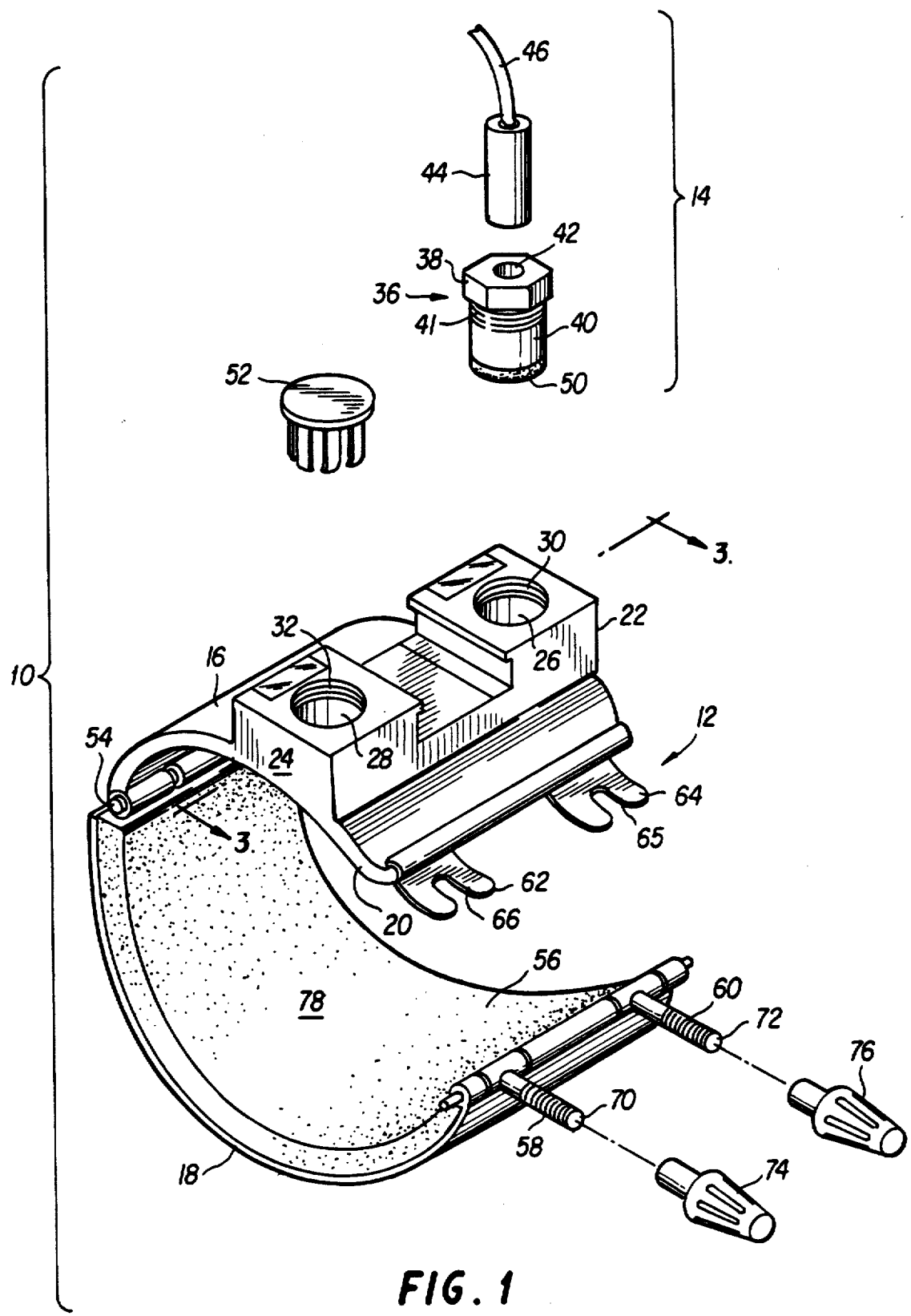
FIG. 1 shows the monitoring apparatus of the present invention in perspective view.

Making reference to FIG. 1, the preferred embodiment of the present invention is shown. The blood pressure monitoring apparatus 10 consists of a holder assembly 12 and a sensing monitor assembly 14.

The holder assembly 12 consists of an upper support base 16, and a lower retaining structure 18, for encircling the wrist of a user and retaining the upper support base 16 in a substantially fixed position relative to the wrist of the user.

The upper support base 16 has an arched support portion 20 conforming to the arch of the wrist. The upper support base 16 is approximately ¼ inch thick, about 2 inches wide and about 2 inches long. In the preferred embodiment it is formed of a substantially rigid plastic material. The width of the upper support base 16 assists in maintaining the monitoring apparatus 10 in a relatively fixed position, resisting torque or twisting.

Projecting from the upper support base 16 are two transducer receiving fittings 22 and 24 on the convex side of the support base 16. The projections 22 and 24 are shown as substantially rectangular, but could be of any configuration. The fittings 22 and 24 have a circular opening therein 26 and 28 that extend through the support base 16.

The openings 26 and 28 of projections 22 and 24 are positioned off center on the support base 16 in a position so that when on the wrist of the user, is centered over the radial artery of either hand.

The openings 26 and 28 are also positioned relative to the support base 16 so that when the support base 16 is on the left wrist, one opening 26 is over the radial artery of the patient proximate the joint of the wrist, and when on the right wrist (after being turned around), the other opening 28 is again over the radial artery of the user proximate the joint of the wrist.

The openings 26 and 28 are approximately ½ inches in diameter and have an internal threaded portion 30 and 32 for receiving a thread 34 associated with the sensing monitor assembly 14.

Figure 3:
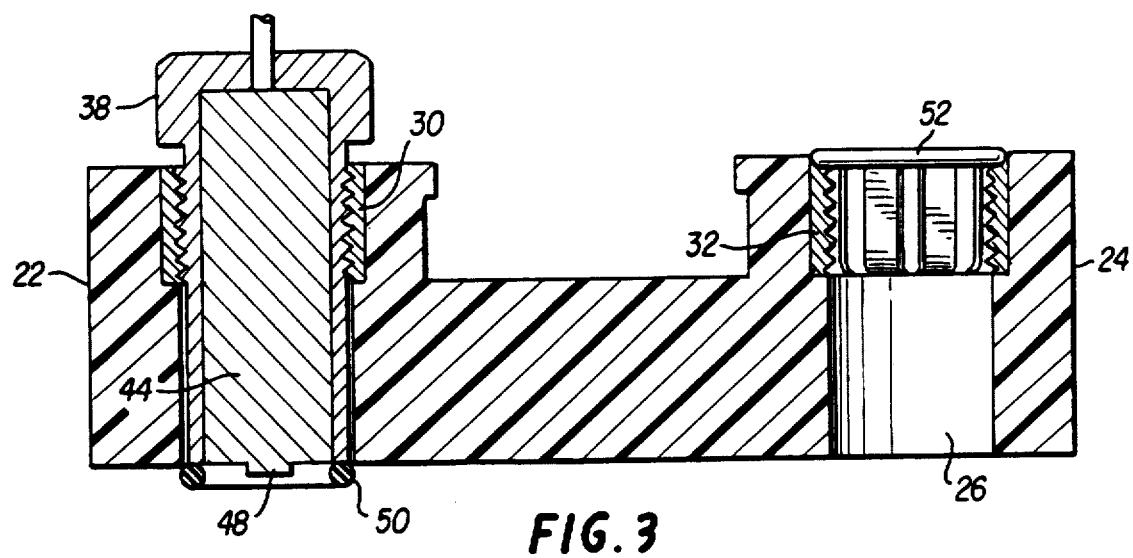
FIG. 3 is a sectional view of the monitoring apparatus.

The sensing monitor assembly 14 is shown in detail in FIG. 1 and in cross-section in FIG. 3. The assembly 14 comprises a sensor housing 36 having a head portion 38 having an outer diameter larger than the diameter of the openings 26 and 28, and a depending cylindrical portion 40 with a threaded portion 41 along a portion adapted to engage the threads 30 and 32 within the openings 26 and 28.

The housing 40 has a longitudinal opening 42 for receiving a strain gauge or transducer 44, which in the preferred embodiment is a commercially available pressure transducer such as are available from Koenigsberg Instruments, Trans America Corp. or Gould, Inc., all of which are responsive to pressure applied to one surface. Other pressure or displacement measuring apparatus may be used as well. The output of the transducer is connected by wire 46 to conventional analog recording equipmment (not shown).

The sensor monitoring assembly 14 has fixed around and below the lower active surface 48 of the transducer 44 a ring 50 that serves as an isolation ring and causes a small portion of the skin in the area above the radial artery to be formed into a bubble that is brought into contact with the surface 48 of the pressure transducer 44. This permits a uniform surface to be presented to the pressure transducer 44.

In the preferred embodiment the surface of the transducer 48 in contact with the skin has a diameter of approximately one-fifth of the diameter of the isolating ring 50. This permits the transducer surface 48 to maintain a more uniform relationship with the skin than would otherwise be achieved, increasing accuracy while at the same time increasing comfort to the user.

In addition, the ring 50 serves to isolate the portion of skin in contact with the pressure transducer 44 from extraneous noise in the body, such as caused by movement of the body, eliminating the need for the various complex compensatory measurement devices.

The sensor monitor assembly 14 is fitted within one or another of the two fittings 22 and 24 depending on whether the monitoring apparatus is on the left hand or the right. A cap 52 is fitted over the opening 26 and 28 in use.

The holder assembly 12 is connected at one end to the lower retaining structure 18 in a pivotable manner about pivot 54, permitting the restraining structure 18 to pivot sufficiently so as to permit the monitoring apparatus 10 to fit around the wrist of the user.

The lower retaining structure 18 is substantially arcuate 56 so as to conform to the shape of the outer portion of the wrist of the user. The size of the opening formed between the arcuate portion 20 of the upper support base 16 and the arcuate portion 56 of the retaining structure 18 is such as to approximately the size of the wrist of an adult patient.

The other end of the retaining structure 18 away from the pivoting end is adjustably fixed to the end of the upper support base 16 opposite the pivot 54. In the preferred embodiment, a series of threaded connecting elements 58 and 60 are pivotably connected to the edge of the retaining structure 18 opposite the pivot 54 so as to engage and disengage complementary U-clamps 62 and 64 along a narrowed portion 66 and 68 of the connecting elements. The connecting elements 58 and 60 have threads 70 and 72 for engagement with the internal threads of caps 74 and 76 fitted on the connecting elements 58 and 60. The caps may be threaded downwardly so as to prevent disengagement of the narrow portion of the connecting elements 58 and 60 from the U-clamps 62 and 64 so as to tighten the entire structure around the wrist of the user.

Soft, resilient padding 78, such as foam rubber, is fitted on the arcuate surface of the retaining device 18 to prevent irritation to the skin of the user.

Figure 2:
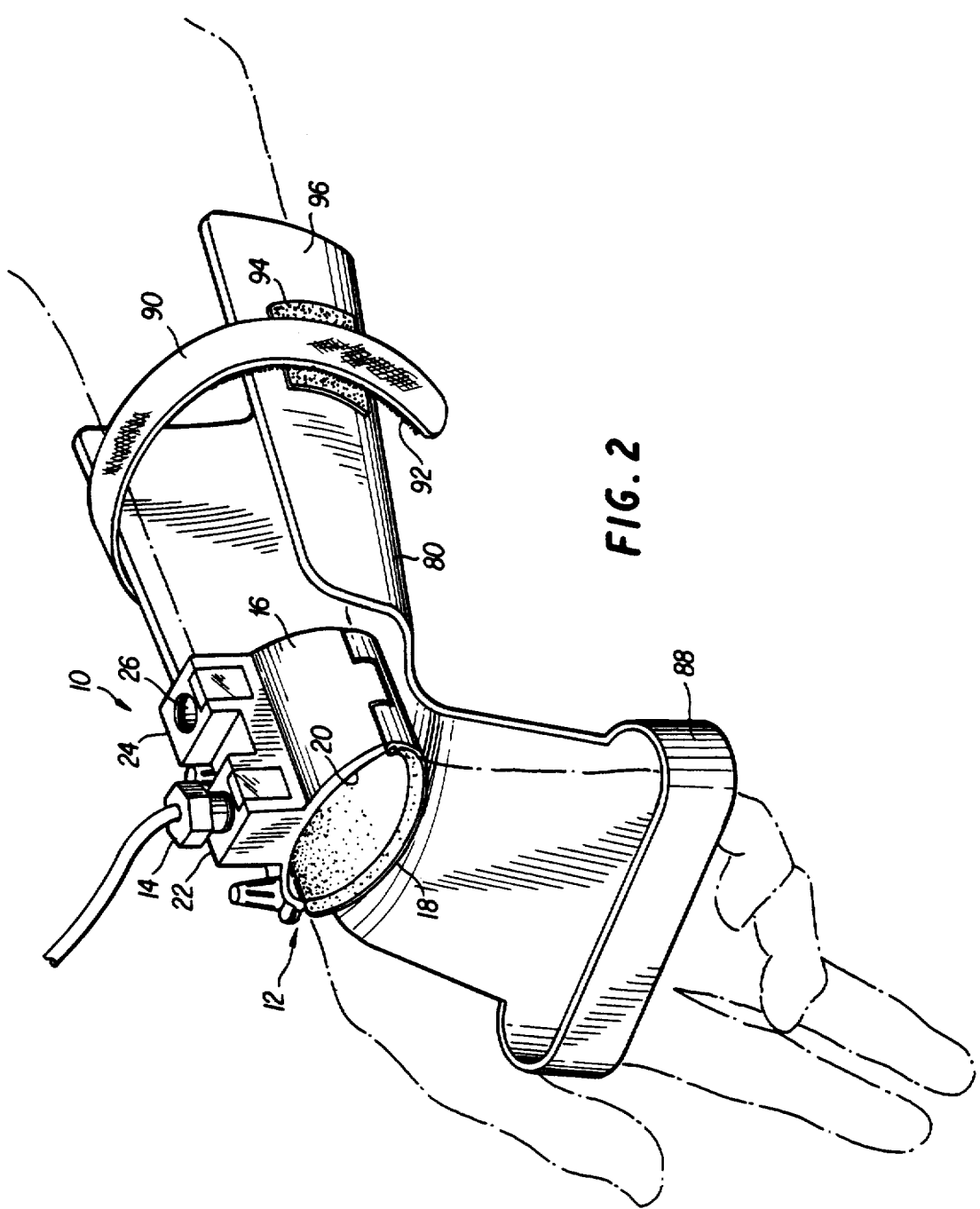
FIG. 2 shows the monitoring apparatus of FIG. 1 and the separate hand and wrist support structure.
Figure 10:
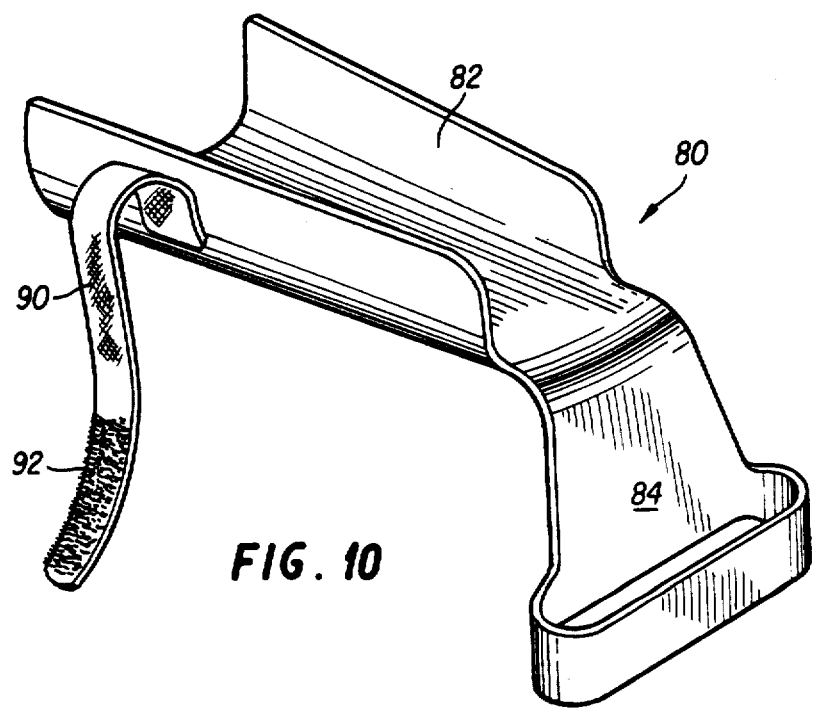
FIG. 10 is a perspective view of the separate hand and wrist support structure.

Used in association with the blood pressure monitoring device is a hand and wrist restraining device 80 shown in FIGS. 2 and 10, which serves to restrain the user from moving his hand relative the wrist, thereby further reducing the introduction of noise into the system, as well as causing the radial artery to be thrust upwardly to the outer surface of the wrist.

The hand restraining device 80 has a forearm channel 82 for receiving the forearm of the patient. The channel 82 may be tapered to conform to the shape of the forearm. The lower end of the restraining device 80 has a hand holding apparatus 84 formed of a depending channel 86 depending at an angle of about 20 degrees from the forearm channel, including a handle 88 through which the fingers and palm of the hand of the user are passed, so that the hand is held at a fixed position, flexed backwards. The hand restraining device is usable with either hand.

A strap 90 having a removable connector element 92, adjusted to fit to the second portion of a connector element 94 attached to the outside wall 96 of the channel 82. In the preferred embodiment the connectors are Velcro band type connectors.

In operation of the device, the monitoring apparatus 10, in its open position, is fitted around the wrist of the user with the holder assembly 12 oriented so that the openings 26 and 28 are oriented over the radial artery of the selected wrist. The connecting elements are engaged and the caps initially tightened.

The hand is then placed in the handle 28 of the hand restraining device, with the fingers and palm through the opening in the depending portion. The forearm is then placed in the channel and held in place by the strap.

The wire form transducer element is then connected to the analog recorder and the monitoring assembly 14 turned until the transducer face is in contact with the surface of the skin isolated by the isolating ring. The monitoring assembly is tightened sufficiently so that the base line on the recording unit is at the desired level. The desired level is where the displayed amplitude on the recorder is at its maximum, thereby indicating the lack of any occlusion of the artery. Continual monitoring of the blood pressure is now possible over a sustained period of time, without discomfort to the patient or occlusion of the radial artery.

Figure 8:
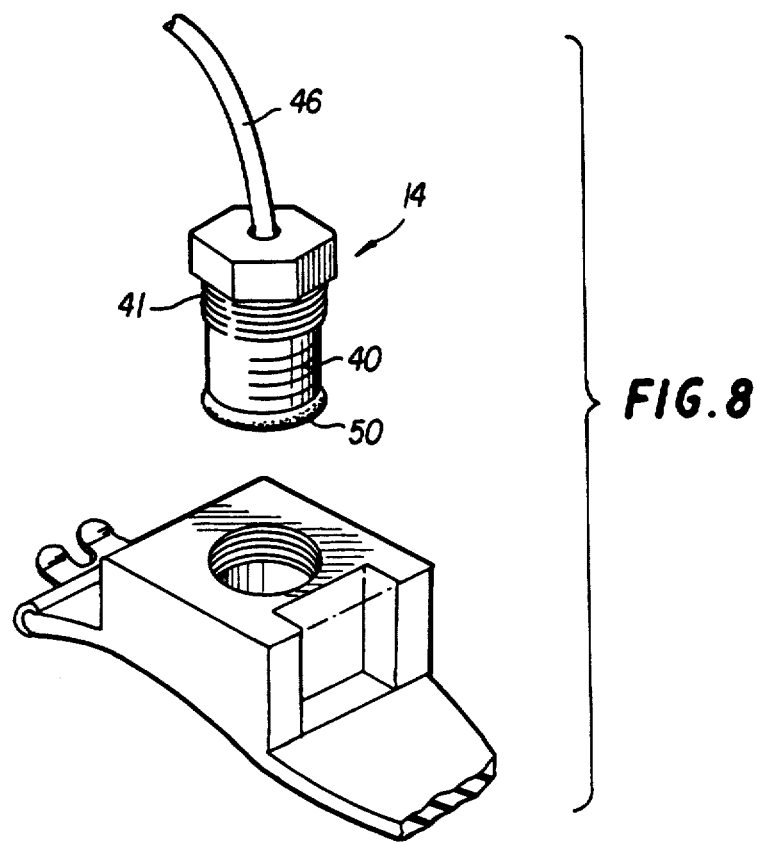
FIG. 8 is an alternate embodiment of the monitoring apparatus in which a single port is used.
Figure 4:
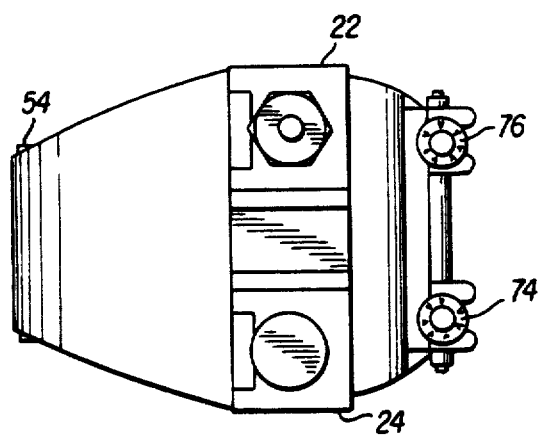
FIG. 4 is a top view of the monitoring apparatus of FIG. 1 in closed position.
Figure 6:
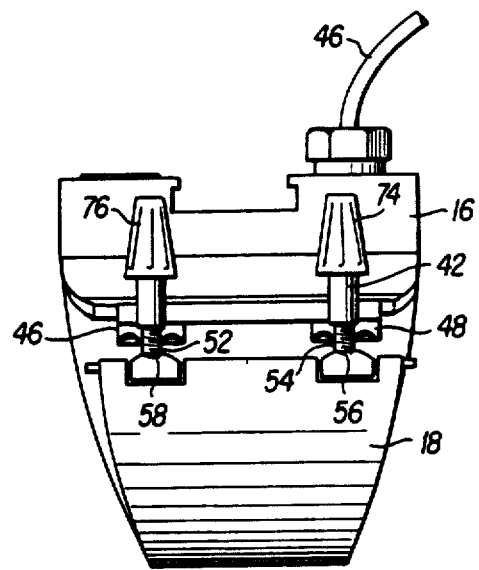
FIG. 6 is a front view of the monitoring apparatus of FIG. 1.
Figure 5:
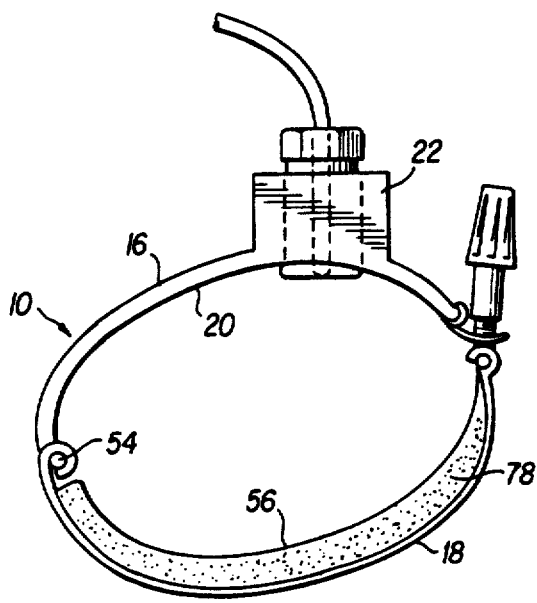
FIG. 5 is a right side view of the monitoring apparatus of FIG. 1.
Figure 7:
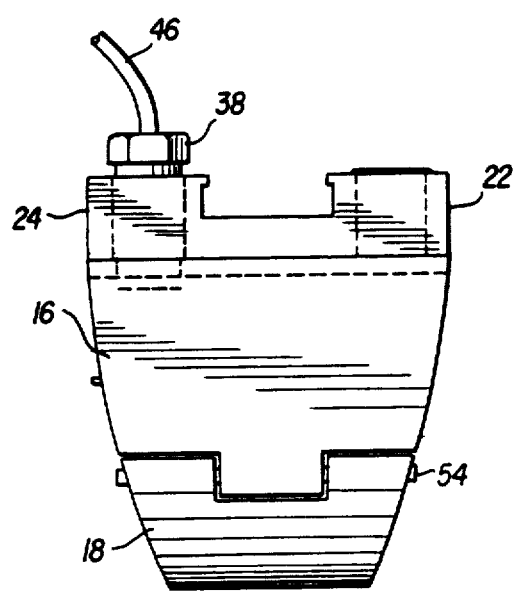
FIG. 7 is a rear view of the monitoring apparatus of FIG. 1.

While the preferred embodiment was designed to have the support plate wide enough to provide a stable base and at the same time permit the transducer 14 to be fixed over a point close to the joint of the wrist, it is recognized that a structure having a single fitting, such as shown in FIG. 8, can be employed by having a narrower support base. This may sacrafice the rigidity supplied by a the wide support base.

Figure 9:
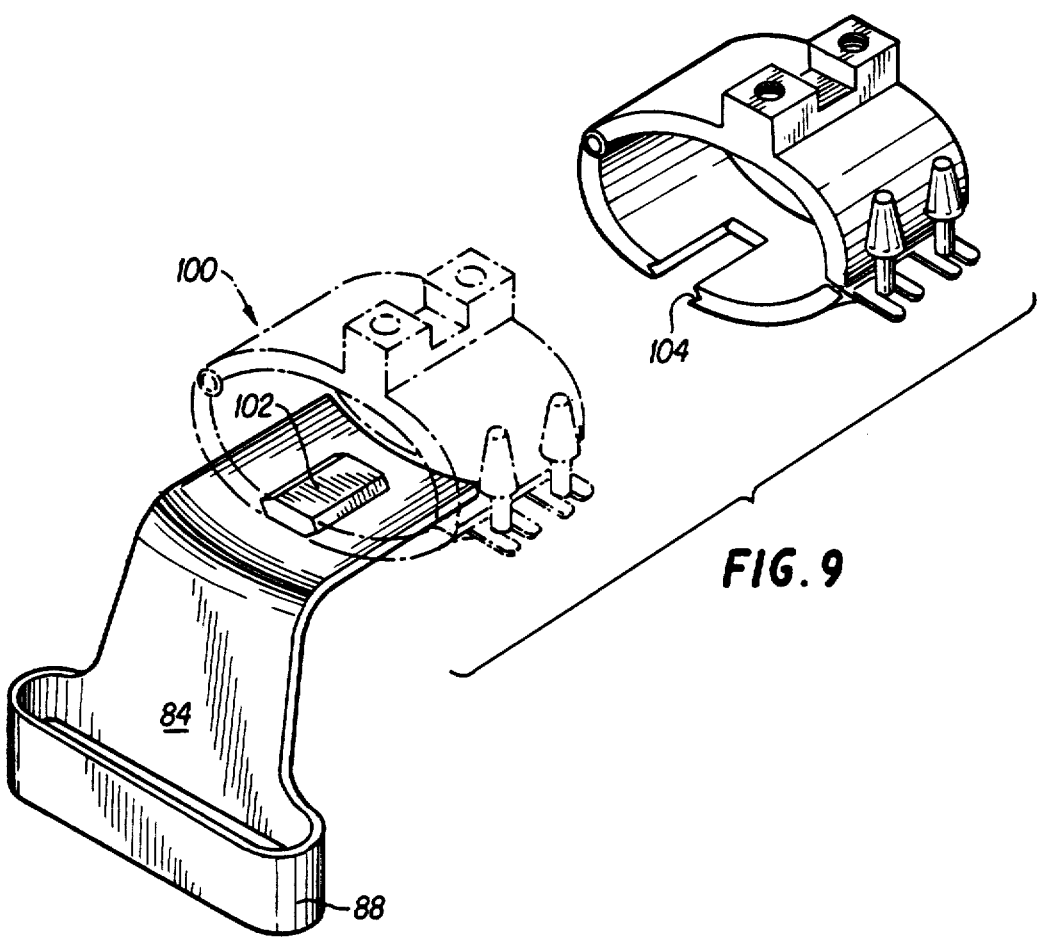
FIG. 9 is an alternative embodiment of a monitor with an integral hand and wrist support structure.

It is also possible to have the arm supporting structure integral with the holder 100 such as illustrated in FIG. 9. In this instance, the pressure monitoring apparatus can be removably attached, such as by a tongue 102 and groove 104 structure, or by a rotatable coupling, or other means for reversing the orientation of the holder relative to the hand restraining device.

While the preferred device employs a pressure sensing device, other conventional sensory devices may be employed which would indicate changes in the volume or pressure in the artery.

It is recognized that other variations and embodiments can be employed without departing from the disclosed invention.

What is claimed is:

1. Blood pressure monitoring apparatus for measuring the pressures in an isolated portion of skin in the vicinity of an artery, comprising:
   a. at least one sensing means having an active surface;
   b. a means for retaining at least one of said transducer sensing means against the skin;
   c. said transducer means having an annular isolating ring surrounding said transducer sensing means for isolating a portion of the skin, said isolating ring having a width small in relationship to the inner diameter of said annular isolating ring so as to prevent flattening of the skin in the vicinity of said transducer and causing a raised portion of skin to form within said isolating ring;
   d. the output of the transducer sensing means being responsive to changes in pressure in said raised portion of isolated skin.

2. The apparatus of claim 1 in which said transducer sensing means comprises a pressure sensitive transducer.

3. The apparatus of claim 1, in which said retaining means, includes a wrist encircling means for holding said transducer sensing means in contact with the skin proximate an artery.

4. The apparatus of claim 3 in which said transducer sensing means comprises a pressure transducer.

5. The apparatus of claim 3 including a hand restraining means for maintaining the hand and forearm fixed relative one another, said hand restraining means being connected to said retaining means.

6. The apparatus of claim 5 in which said hand restraining means is integrally connected to said blood monitoring apparatus.

7. The apparatus of claim 6 in which said hand restraining means is movably fixed to said sensing means.

8. The apparatus of claim 5 in which said hand restraining means restrains the hand at an open position of approximately 20 degrees in relation to the forearm.

9. The apparatus of claim 3 including two openings in the wrist encircling means aligned along a position over the radial artery proximate the wrist, depending on whether the device is used on the right wrist or the left wrist.

10. The apparatus of claim 1 in which the annular isolating ring has a diameter substantially larger than the diameter of the active surface of the transducer adapted to be sensing means in contact with the isolated skin.

11. The apparatus of claim 10 in which said isolating ring has an inner diameter at least twice that of the diameter of the active surface of the transducer sensing means.

12. The apparatus of claim 10 in which the inner diameter of the isolating ring is approximately six (6) times the diameter of the active surface of the transducer sensing means.

13. The apparatus of claim 10 in which said isolating ring has an inner diameter at least twice that of the diameter of the active surface of the transducer sensing means, the isolating ring creating an isolated raised dome portion of skin surrounded by said isolating ring, said transducer sensing means sensing the changes of pressure in the isolated raised dome portion of skin.

14. The apparatus of claim 1 in which the width of the annular isolation ring is substantially smaller than the diameter of the opening in said annular isolation ring.

15. Blood pressure monitoring apparatus comprising:
    a. at least one transducer sensing means;
    b. a means for retaining at least one of said transducer means against the skin;
    c. said transducer means having an annular isolating ring surrounding said transducer sensing means for isolating a portion of the skin, said isolating ring having an inner diameter at least twice that of the diameter of the active surface of the transducer sensing means coming in contact with said isolated portion of skin so as to prevent flattening of the skin in the vicinity of said transducer and causing a raised portion of skin to form within said isolation ring.

16. Blood pressure monitoring apparatus comprising:
    a. at least one transducer sensing means;
    b. a means for retaining at least one of said transducer sensing means against the skin, said retaining means including a wrist encircling means for holding said transducer sensing means in contact with the skin proximate an artery;
    c. Said transducer means having an annular isolating ring surrounding said transducer sensing means for isolating a portion of the skin, said isolating ring having a width small in relationship to the inner diameter of said isolating ring causing a raised portion of skin to form within said isolation ring;
    d. the output of the transducer sensing means being responsive to changes in pressure in said raised portion of skin; and
    e. a hand retaining means integrally connected to said blood pressure monitoring apparatus for restraining the hand at an open position of approximately 20 degrees in relation to the forearm.

17. Blood pressure monitoring apparatus comprising:
    a. at least one transducer sensing means;
    b. a means for retaining at least one of said transducer sensing means against skin;
    c. said transducer means having an annular isolating ring surrounding said transducer sensing means for isolating a portion of the skin causing a raised portion of skin to form within said isolation ring, said isolating ring having an inner diameter of approximately six (6) time the diameter of the active surface of the transducer sensing means.
    d. The active surface of said transducer being recessed from the plane of the surface of the isolating ring in contact with the skin, the output of the transducer sensing means being responsive to changes in pressure in said raised portion of skin.

* * * * *